(12) United States Patent
Gowda et al.

(10) Patent No.: US 6,507,747 B1
(45) Date of Patent: Jan. 14, 2003

(54) METHOD AND APPARATUS FOR CONCOMITANT STRUCTURAL AND BIOCHEMICAL CHARACTERIZATION OF TISSUE

(75) Inventors: Ashok Gowda, College Station, TX (US); Roger McNichols, Bryan, TX (US); Massoud Motamedi, Houston, TX (US)

(73) Assignees: Board of Regents, The University of Texas System, Austin, TX (US); BioTex, Inc., Houston, TX (US)

( * ) Notice: Subject to any disclaimer, the term of this patent is extended or adjusted under 35 U.S.C. 154(b) by 0 days.

(21) Appl. No.: 09/449,803

(22) Filed: Nov. 26, 1999

Related U.S. Application Data
(60) Provisional application No. 60/110,599, filed on Dec. 2, 1998.

(51) Int. Cl.[7] .................................................. A61B 5/00
(52) U.S. Cl. ......................... 600/407; 600/473; 600/478
(58) Field of Search ................................. 600/407, 473, 600/478, 475, 476, 477; 356/345, 346

(56) References Cited

U.S. PATENT DOCUMENTS

| | | | | |
|---|---|---|---|---|
| 5,921,926 A | * | 7/1999 | Rolland et al. | 600/407 |
| 6,002,480 A | * | 12/1999 | Izatt et al. | 356/479 |
| 6,134,003 A | * | 10/2000 | Tearney et al. | 356/450 |
| 6,141,577 A | * | 10/2000 | Rolland et al. | 600/407 |

* cited by examiner

*Primary Examiner*—Marvin M. Lateef
*Assistant Examiner*—Eleni Mantis Mercader
(74) *Attorney, Agent, or Firm*—Mueting, Raasch & Gebhardt, P.A.

(57) ABSTRACT

An optical imaging probe for providing information representative of morphological arid biochemical properties of a sample is provided. The optical imaging probe includes a spectroscopic imaging probe element and an OCT imaging probe element.

38 Claims, 2 Drawing Sheets

METHOD AND APPARATUS FOR CONCOMITANT STRUCTURAL AND BIOCHEMICAL CHARACTERIZATION OF TISSUE

RELATED APPLICATION DATA

This application claims priority to provisional patent Application Ser. No. 60/110,599, filed Dec. 2, 1998.

BACKGROUND OF THE INVENTION

The present invention is directed to a technique and apparatus for obtaining morphological and biochemical information from a sample site. More particularly, the present invention is an optical probe, system and technique of sequentially or concurrently acquiring morphological and biochemical information from a sample site to more quickly, reliably and efficiently analyze and characterize the status (e.g., pathological, morphological, biochemical, and physiological state) of the suspicious tissue (e.g., a lesion, tumor, or plaque) within the site.

Current methods for screening and diagnosis of pathologic conditions in tissue such as cancer often involve surgical biopsy of the tissue followed by histological evaluation. This procedure is not only invasive, time-consuming and expensive but often is not capable of rapid and reliable screening of a large surface such as that of the oral cavity. Since early diagnosis and treatment tend to be critical to effective and successful treatment of these pathologies, the development of better techniques and devices for diagnosis and screening would result in improved clinical outcomes.

Non-invasive optical methods, such as fluorescence spectroscopy, for the detection of certain biochemical changes associated with early neoplastic development have been described. These techniques are particularly sensitive to malignant tissue transformation. However, such techniques are limited in wide spread adoption because they are unable to provide information with regard to the morphology of the tissue and, as such, often result in a "false positives."

Optical coherence tomography (OCT) is a non-invasive imaging modality which allows high resolution of tissue microstructure imaging with resolution on the order of microns. This technique measures detailed changes within a few millimeters of a non-transparent tissue structure. The currently the primary shortcoming of the OCT imaging modality is the time required to obtain images over a sufficient area.

Boppart et al., "Forward Imaging Instruments for Optical Coherence Tomography" Optics Letters, Vol.22(21): 1618–1620 (1997) describes a technique and device which employs endoscopic and OCT imaging modalities. In this regard, Boppart et al. employs a conventional endoscope having a white light illumination source, in a conventional manner, to visually inspect the target tissue. Boppart et al., after detecting suspicious tissue (for example, on a suspicious polyp or bump or discolored spot) within the target, employs an OCT imaging device to further study the suspicious tissue. Boppart et al., however, directs the OCT probe onto that tissue using the white light (light which is visible to the human) image.

Importantly, Boppart does not employ a "fluorescence image" to guide the OCT probe to the suspicious tissue within the target. Fluorescence imaging is a sensitive optical modality for detecting the presence of suspicious tissues (for example, cancers and other biochemical processes) before the appearance of any visual cues—that is cues which are visible to the human eye via white light. In addition, fluorescence photons may originate from points below the surface of the target thereby enhancing the likelihood of identifying suspicious tissue well before the appearance of any visual evidence of, for example, cancer.

The present invention improves on the Boppart et al. technique and device by incorporating a means for obtaining biochemical information directly through spectroscopic imaging or sensing. In this regard, the present invention employs a fluoroscopic, near infrared (NIR) absorption spectroscopic, NIR reflectance spectroscopic, Raman spectroscopic, and/or magnetic resonance spectroscopic approach to detect suspicious tissue within a target sample and, upon detecting the suspicious tissue, employs OCT to study the morphology of the tissue in detail. Thus, the present invention combines OCT with a technique and means for obtaining spectroscopic information as well as visual information concurrently or sequentially from the same site. The present invention may be employed, for example, whenever spectroscopic and morphological information are desired or necessary. The techniques and devices of the present invention may be applied in the medical field including such applications as: (1) cancer detection and differentiation of benign lesions from pre-malignant and malignant lesions as well as staging of superficial tumors; (2) detection and classification of atherosclerotic plaques; (3) monitoring tissue changes; (4) intraoperative means for assessing tissue removal and for administration of drugs; (5) monitoring pharmacokinetic drug distribution as a function of morphology; (6) intraoral examination of dental tissues (hard and soft); and (7) monitoring changes in tissue (e.g., the cervix) architecture and bio-composition following treatments or during pregnancy.

It should be noted that the techniques and devices of the present invention may also be employed in such situations where simultaneous OCT imaging and optical spectroscopic information are desirable, such as materials characterization, plant physiology, and industrial process monitoring.

Thus, there is a need for a technique and apparatus to investigate and image the morphological and biochemical properties in the first few millimeters of a biological structure with a high degree of spatial resolution to facilitate the analysis of the pathological, morphological and physiological state of the structure. There is a need for a method and device to provide regional biochemical information followed by a closer more detailed inspection of the tissue structure. The invention described herein provides a highly sensitive, specific, and rapid means of non-invasive identification of potentially cancerous lesions based on spectroscopic measurement as well as a means for more detailed morphologic characterization using OCT to image the tissue architecture and spectroscopy to image the biochemical content or status of the tissue.

SUMMARY OF THE INVENTION

In a first aspect, the present invention is an optical imaging probe to provide information representative of morphological and biochemical properties of a sample (e.g., cancerous tissue). The optical imaging probe may include a spectroscopic imaging probe element, an OCT imaging probe element, an optical probe window, and a reflective optical filter. The reflective optical filter may be disposed within an optical path between the optical window and the spectroscopic and OCT imaging probe elements and positioned to receive radiation incident on the optical probe window and to provide radiation of a first wavelength to the spectroscopic imaging probe element and to provide radiation of a second wavelength to the OCT imaging probe element. The optical probe of this aspect of the invention facilitates sequential or concomitant OCT imaging and spectroscopic (e.g., fluoroscopic) imaging.

Moreover, the OCT information and the spectroscopic information is obtained sequentially or concomitantly without movement of the OCT/spectroscopic probe relative to the sample under investigation. That is, morphologic and biochemical related information is obtained of the sample without movement of the OCT/spectroscopic probe. This facilitates accurate registration between the OCT image and the spectroscopic image. Thus, a relatively large area (e.g., the oral cavity) may be rapidly and non-invasively scanned for biochemical anomalies and morphological characteristics of those anomalies with precise registration.

In a second principle aspect, the present invention is an imaging system which includes a spectroscopic imaging system, an OCT imaging system, a data analysis unit, and an OCT/spectroscopic imaging probe. In this aspect, the OCT/spectroscopic imaging probe includes a spectroscopic imaging probe element to facilitate imaging using a spectroscopy imaging technique, an OCT imaging probe element to facilitate an OCT imaging technique, and a reflective optical filter. The reflective optical filter is disposed within an optical path between an optical window of the OCT/spectroscopic imaging probe and the spectroscopic and OCT imaging probe elements. In addition, the reflective optical filter is positioned to receive radiation incident on the optical probe window and to provide radiation of a first wavelength to the spectroscopic imaging probe element and to provide radiation of a second wavelength to the OCT imaging probe element so that the OCT/spectroscopic imaging probe allows sequential or concomitant OCT imaging and spectroscopic imaging.

In a preferred embodiment, the spectroscopic imaging system and the OCT system are electrically, optically and/or physically coupled to the data analysis unit. The data analysis unit receives the biochemical and morphological information and allows an operator or physician to analyze that information to assess the pathological, morphological and physiological state of the structure. In this regard, the data analysis unit allows the operator or physician to quickly, reliably and efficiently analyze and characterize the status (e.g., pathological, morphological, biochemical, and physiological state) of the suspicious tissue (e.g., a lesion, tumor, or plaque). This analysis and characterization may be done in real time or off-line.

The spectroscopic imaging system may be fluoroscopic, NIR absorption spectroscopic, NIR reflectance spectroscopic, Raman spectroscopic, magnetic resonance spectroscopic and/or infrared based (i.e., sensing spatial temperature using).

BRIEF DESCRIPTION OF THE DRAWINGS

In the course of the detailed description to follow, reference will be made to the attached drawings, in which.

DETAILED DESCRIPTION

In one aspect, the present invention is a method and apparatus for integrating a spectroscopic (e.g., fluoroscopic) imaging modality with an OCT imaging modality. The technique of the present invention includes scanning the target area using a spectroscopic imaging modality and, upon detecting biological changes in the tissue within the field of view, employing an OCT imaging modality to determine, with a high degree of certainty and a high spatial resolution, the morphological and biochemical properties of the suspect tissue. The spectroscopic and OCT information allow for a detailed analysis of the pathological, morphological and physiological state of the tissue.

The spectroscopic imaging system and technique may be fluoroscopic based, NIR absorption spectroscopic based, NIR reflectance spectroscopic based, Raman spectroscopic based, magnetic resonance spectroscopic based and/or infrared based (i.e., sensing spatial temperature using, for example, IR imaging camera). Thus, the present invention employs the spectroscopic imaging modality to provide critical information relating to biological changes in tissues. Where the spectroscopic imaging modality is fluoroscopic based, the biochemical information obtained is sensitive to any changes (both at the surface as well as below the surface) whether the changes are significant or not. However, these instruments scan a large target area (for example, a patient's oral cavity) rapidly.

The present invention employs the OCT imaging modality to provide detailed information relating to changes in the morphological and biochemical properties of the tissue. Because OCT imaging systems include a field of view on the order of 2-3 mm, the present invention implements the OCT imaging modality (concurrently or sequentially) when the spectroscopic imaging modality detects biological changes in the tissue. As such, although OCT imaging systems are relatively slow, albeit with high resolution, the present invention implements the OCT imaging system when the spectroscopic imaging system detects a change in the biological characteristics of the target area (for example the patient's oral cavity). In this regard, the spectroscopic imaging system is sensitive to significant and non-significant changes (both at the surface as well as below the surface) in biological characteristics. The present invention relies upon or employs the OCT imaging system to provide additional information, having a high degree of confidence, as to whether the biological changes are significant.

Figure 1:
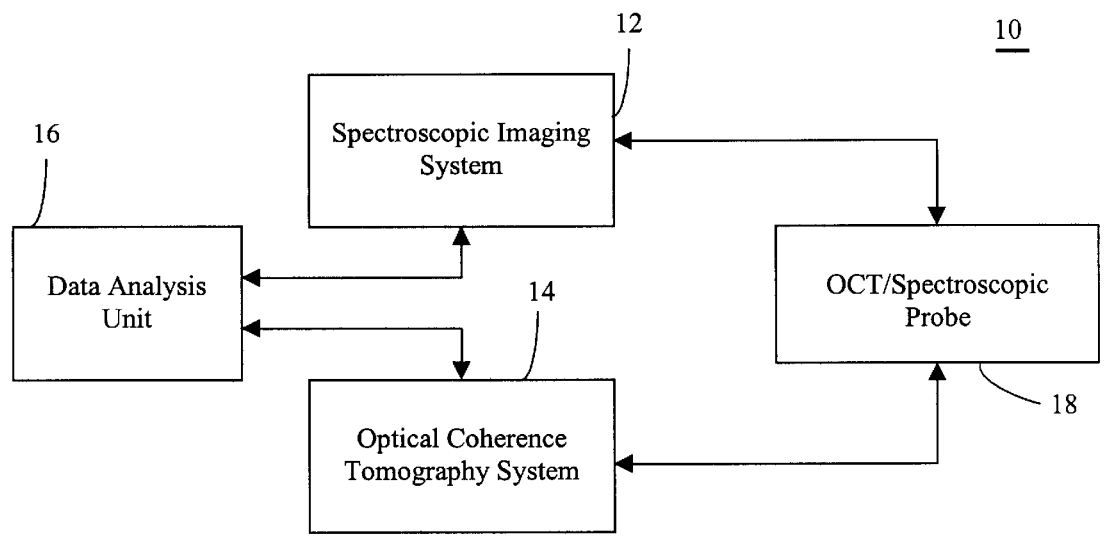
FIG. 1 is a block diagram of one aspect of the present invention.

With reference to FIG. 1, the imaging system 10 of the present invention includes a spectroscopic imaging system 12, an OCT imaging system 14, a data analysis unit 16 and a OCT/spectroscopic probe 18. The spectroscopic imaging system 12 (e.g., fluoroscopically based) is optically coupled to the OCT/spectroscopic probe 18 to collect biochemical related information measured by the OCT/spectroscopic probe 18. The OCT system 14 is optically coupled to the OCT/spectroscopic probe 18 to collect morphologic related information measured by the OCT/spectroscopic probe 18. Both spectroscopic imaging system 12 and the OCT system 14 may be electrically, optically and/or physically coupled to the data analysis unit 16 which collects the biochemical and morphological information for analysis by an operator or physician.

As mentioned above, the spectroscopic imaging system 12 may be fluoroscopic, NIR absorption spectroscopic, NIR reflectance spectroscopic, Raman spectroscopic, and/or magnetic resonance spectroscopic—all of which provide biochemical related information. At times, however, the discussion below focuses on a fluoroscopic technique in an exemplary manner. Where the spectroscopic imaging system 12 employs a fluoroscopic technique, the spectroscopic imaging system 12 implements fluorescence imaging through a gradient refractive index boroscope (for example, Edmund Scientific part no: J54062) with excitation provided by a Xenon arc lamp. The excitation is filtered through an interference filter (for example, Melles-Griot 03F1B002) and coupled to illumination fibers. Emitted light travels through the imaging portion of the endoscope and is filtered by a broadband 650 nm filter (for example, Edmund Scientific part no: H46153) and is detected by a CCD camera with frame integrator.

It is noted, however, that the other spectroscopic imaging modalities may be implemented in the present invention in a manner similar to that described below.

The OCT system 14 may be a commercially available optical coherence tomography system, for example, a system manufactured by Optimec Ltd (OCTI or OTC of Cleveland, Ohio). These type systems are based generally on the principles described and illustrated in U.S. Pat. No. 5,321,501 and 5,459,570, which are incorporated herein by reference. Other commercially available OCT systems are also suitable.

The data analysis unit 16 may be a properly programmed computer having sufficient memory to permit an operator or physician to analyze the biochemical and morphological information obtained by the spectroscopic imaging system 12 and the OCT system 14. The data analysis unit 16 permits the operator or physician to quickly, reliably and efficiently analyze and characterize the status (e.g., pathological, morphological, biochemical, and physiological state) of the suspicious tissue (e.g., a lesion, tumor, or plaque). The analysis and characterization may be done in real time or off-line.

Figure 2:
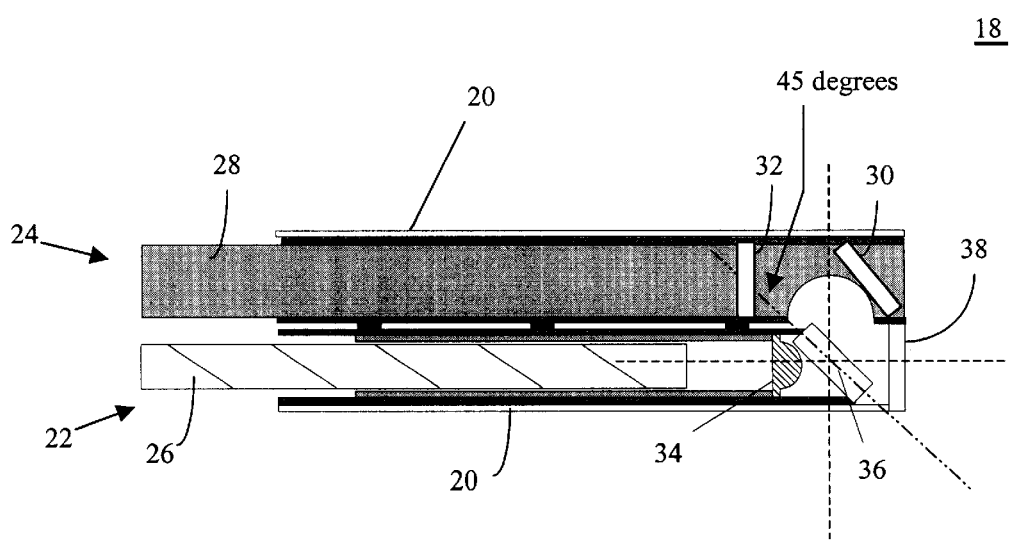
FIG. 2 is a schematic block diagram of one embodiment of an optical probe of FIG. 1.

FIG. 2 illustrates a first embodiment of the OCT/spectroscopic probe 18 of FIG. 1. The OCT/spectroscopic probe 18 of FIG. 2 allows concomitant OCT imaging and fluoroscopic imaging. As such, the OCT imaging system 14 and a spectroscopic imaging system 12 employ probe 18 to assess a tissue under investigation. Moreover, in this embodiment, both OCT information and spectroscopic information of a given sample may be obtained without movement of the OCT/spectroscopic probe 18 relative to the tissue under investigation as well as movement of the optical elements therein. That is, morphologic and biochemical information may be obtained of a tissue without movement of the OCT/spectroscopic probe 18 and without movement of the optical components (lens, filter, mirror, and probe elements 26 and 28) within probe 18. Thus, in operation, the OCT/spectroscopic probe 18 of FIG. 2 may be used to rapidly and non-invasively scan a given sample area for spectroscopically (e.g., fluorescently) detected biochemical anomalies and, without movement of OCT/spectroscopic probe 18, concurrently or subsequently examine suspicious tissue within that area for detailed morphology.

The OCT/spectroscopic probe 18 includes housing 20 containing lumens 22 and 24. Lumen 22 physically secures OCT imaging probe element 26 and lumen 24 physically secures fluoroscopic imaging probe element 28. In this embodiment, fluoroscopic imaging probe element 28 may be a side-looking spectroscopic probe having mirror 30 and spectroscopic window 32.

The OCT/spectroscopic probe 18 further includes aspheric lens 34 and reflective optical filter 36 at a distal end of the probe approximate to probe window 38. In a preferred embodiment, the reflective optical filter 36 is coated to possess dichroic reflective properties such that, when mounted and positioned at a 45 degree angle relative to a vertical axis of the probe window 38, radiation having a wavelength in the near infrared spectrum (greater than 700 nm, for example 1300 nm) travels through the reflective optical filter 36, through the probe window 38; as well as to the sample (not shown) and may travel from the sample, through the probe window 38, through the reflective optical filter 36 to the OCT imaging probe element 26. A suitable optical filter 36 may be for example Precision Glass and Optics (Santa Ana, Calif.) part no: CMF_060.

The dichroic reflective properties of the optical filter 36, although not reflecting energy having a wavelength in the near infrared spectrum when positioned at a 45 degree angle relative to the vertical axis of the probe window 38, is designed to reflect energy having a wavelength in the visible spectrum (e.g., less than 700 nm). As such, radiation having wavelengths in the visible spectrum is reflected by the reflective optical filter 36 onto/from mirror 30 and, in turn, through spectroscopic window 32 and to/from spectroscopic imaging probe element 28. The near infrared radiation, however, is not reflected but rather travels through the reflective optical filter 36 onto/from the aspheric lens 34 and to/from OCT imaging probe element 26.

In a preferred embodiment, OCT probe element 26, aspheric lens 34, reflective optical filter 36 and optical probe window 38 are relatively located or positioned to produce little to no magnification. In this regard, the distance between OCT probe element 26 and aspheric lens 34 is 5.5 mm and the distance between the aspheric lens 34 the optical probe window 38 is 5.5 mm. Should magnification be desired, these relative distances may be adjusted accordingly. Additionally, the need for the aspheric lens 34 may be obviated if, for example, the OCT imaging probe element 26 is constructed such that the focal plane coincides with the probe window 38. It should be noted that the aspheric lens 34 used in the preferred embodiment may be replaced with any suitable focusing optic.

It should be noted that, in a preferred embodiment, the aspheric lens 34 has a diameter of 4 mm at its base and a spheroid diameter of 3.6 mm. The focal length of the lens 34 is 2.75 mm.

In a preferred embodiment, the spectroscopic imaging is fluorescence based. Under this circumstance, the spectroscopic imaging system 12 (FIG. 1) implements fluorescence imaging through a gradient refractive index boroscope (for example Edmund Scientific part no: J54062) with excitation provided by a Xenon arc lamp. The excitation is filtered through an interference filter (for example Melles-Griot 03F1B002) and coupled to illumination fibers. Emitted light travels through the imaging portion of the endoscope and is filtered by a broadband 650 nm filter (for example Edmund Scientific part no: H46153) and is detected by a CCD camera with frame integrator.

In operation, the biochemical information contained in the radiation incident on optical probe window 38 is reflected by reflective optical filter 36 to mirror 30 and onto spectroscopic imaging probe element 28. Concurrently or sequentially, upon detection of an "abnormal" image indicating suspicious tissue, the operator may examine that tissue using the OCT imaging system 14. In this regard, without moving the OCT/spectroscopic probe 18, the operator may initiate OCT imaging by enabling the OCT imaging probe element 26 to collect morphological information.

Thus, OCT/spectroscopic probe 18 of FIG. 2 may be employed to rapidly and non-invasively scan an area for spectroscopically-detected biochemical anomalies using spectroscopic (e.g., fluorescence) imaging (via probe element 28, spectroscopic imaging system 12, and data analysis element 16) and simultaneously examine detailed morphology of any suspicious tissue (via probe element 26, OCT system 14 and data analysis element 16). The configuration of the optical elements in the OCT/spectroscopic probe 18, including reflective optical filter 36 placed in the lumen of the probe 18, allows an operator to simultaneously image using OCT and fluorescence. The OCT/spectroscopic probe 18 allows simultaneous fluorescence images to be taken and OCT scans to be performed through imaging window 32 without movement of OCT/spectroscopic probe 18 relative to the tissue under investigation and without movement of optical components in the OCT/spectroscopic probe 18. As such, consistently accurate registration between the OCT image and the spectroscopic image is maintained.

It should be noted that, in a preferred embodiment, the spectroscopic imaging probe is an endoscope and the spectroscopic imaging system is fluoroscopic based. As such, the fluoroscopically obtained biochemical information is sensitive to biochemical changes both at the surface as well as below the surface.

Moreover, it should be noted that the combined probe may be constructed in a manner such that visible or ultraviolet radiation is used for OCT imaging and longer wavelengths are used to obtain to obtain spectroscopic information. Such embodiments may be implemented by modifying the filtering characteristics and/or wavelength selectivity of the reflective optical filter 36.

Figure 3:
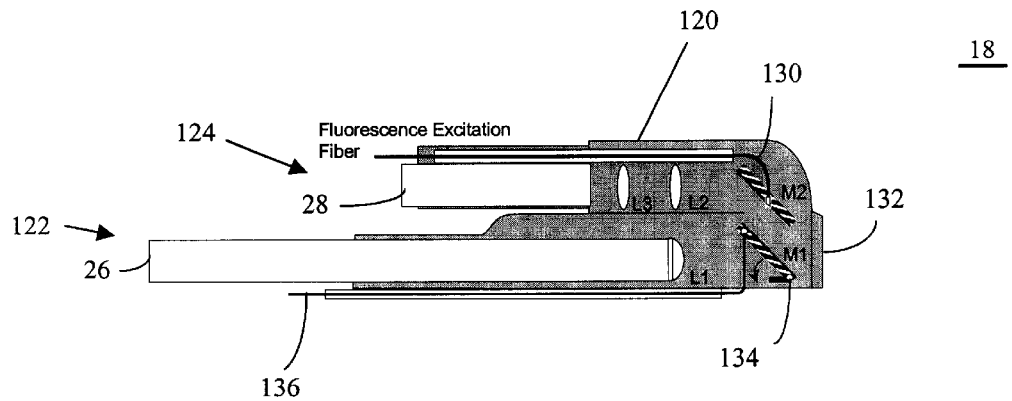
FIG. 3 is a schematic block diagram of another embodiment of an optical probe of FIG. 1.

FIG. 3 illustrates a second embodiment of the OCT/spectroscopic probe 18 of FIG. 1. FIG. 3 is described in connection with a fluoroscopic based spectroscopic imaging system 12. With that in mind, similar to embodiment of FIG. 2, the OCT/spectroscopic probe 18 of FIG. 3 integrates OCT imaging techniques and fluoroscopic imaging techniques. The spectroscopic imaging system 12 and the OCT imaging system 14 employ the same physical probe to collect information relating to biochemistry and morphology. Moreover, as with the probe of FIG. 2, the OCT information and the spectroscopic information may be obtained sequentially without movement of the OCT/spectroscopic probe 18 relative to the tissue under investigation. That is, morphologic and biochemical related information may be obtained of a given section of tissue without movement of the OCT/spectroscopic probe 18. This facilitates accurate registration between the OCT image and the spectroscopic image. Under this circumstance, a relatively large area (e.g., the oral cavity) may be rapidly and non-invasively scanned for biochemical anomalies and morphological characteristics of those anomalies with precise registration.

With reference to FIG. 3, the OCT/spectroscopic probe 18 includes housing 120 containing lumens 122 and 124. The lumen 122 is used to house OCT imaging probe element 26. The lumen 124 provides a housing for the fluoroscopic imaging probe element 28.

OCT/spectroscopic probe 18 further includes mirrors M1 and M2 at a distal end of the probe. Mirrors M1 and M2 are mounted and configured in a periscope fashion. A fluorescence excitation fiber 130 resides in a hole located in the center of the mirror M2. Fluorescence excitation fiber 130 provides excitation light to the sample under investigation.

Light from the fluorescence excitation fiber 130 is directed to the sample by the mirror M1. Here, mirror M1 reflects the excitation light from the fluorescence excitation fiber 130 through probe imaging window 132 located at a distal end of OCT/spectroscopic probe 18.

The mirror M1 is mounted on hinge 134 to permit movement in a manner which permits selective imaging by either OCT imaging probe element 26 or fluoroscopic imaging probe element 28 through probe imaging window 132. In one embodiment, mirror M1 is connected to cable 136 such that when placed under sufficient tension (directly or indirectly) by an operator, mirror M1 moves or pivots about hinge 134 to permit OCT imaging to be performed through the same imaging window as fluoroscopic imaging. As such, the OCT/spectroscopic probe 18 permits collection of biochemical and morphologic information without movement of probe 18.

Fluorescence imaging is conducted when mirror M1 is in an "up" or vertical position. Under these circumstances, mirrors M1 and M2 form a periscope-like optical imaging path. Excitation light at 400 nm (±30 nm) is provided by a 150 Watt Xenon arc lamp (not shown) which is filtered through an interference filter (Melles-Griot 03F1B002, not shown) and lens coupled to fluorescence excitation fiber 130 (e.g., a 400 $\mu$m optical fiber). The distal end of excitation fiber 130 is mounted in a small hole in the center of mirror M2 and illuminates the tissue area to be probed. Reflected and fluorescent light is imaged though mirrors M1 and M2 periscope-like optical path onto the face of a gradient refractive index (GRIN) rod relays (not shown). The GRIN rod relays the image to the spectroscopic imaging system having magnification and filtering optics (not shown). The magnified and filtered image may be analyzed, displayed and recorded by data analysis element 16 which includes a 512×512 TE-cooled CCD camera, e.g., Princeton Instruments/E.G.&G 1530PUV (not shown).

OCT imaging is performed by placing mirror M1 in a "down" or horizontal position. Under these circumstances, mirror M1 is not in the optical path and, as such does not form a periscope-like imaging path with mirror M2. Mirror M1 is placed in A) the down position using cable 136. Here, direct OCT imaging of a suspicious area is conducted using the endoscopic OCT imaging probe (Optimec Ltd.). The OCT imaging probe element 26 uses a piezoelectric galvanometer (not shown) to laterally translate a probe arm of a single mode, polarization-maintaining fiber optic Michelson interferometer and has a field of view which is approximately 2 mm in the lateral direction and 1.5 mm in the depth direction.

In operation, upon detection of an "abnormal" fluorescence image indicating a suspicious tissue, the area may be immediately examined by OCT imaging. Without moving the OCT/spectroscopic probe 18, the operator may initiate OCT imaging by moving or causing to move cable 136 such that the mirror M1 moves to a "down" position. With the mirror M1 in the "down" position, OCT imaging via OCT imaging probe element 26 is possible. Thus, OCT/spectroscopic probe 18 may be employed to rapidly and non-invasively scan an area for fluorescently-detected biochemical anomalies using fluorescence imaging and to subsequently examine, via OCT imaging, the detailed morphology of any suspect tissue within the area. Mirror M1 placed in the lumen of the OCT/spectroscopic probe 18 allows an operator to switch between fluorescence imaging to OCT imaging by manipulation (directly or indirectly) of cable 136. OCT/spectroscopic probe 18 allows sequential fluorescence images to be taken and OCT scans to be performed through imaging window 132 without movement of OCT/spectroscopic probe 18 relative to the tissue under investigation.

Figure 4:
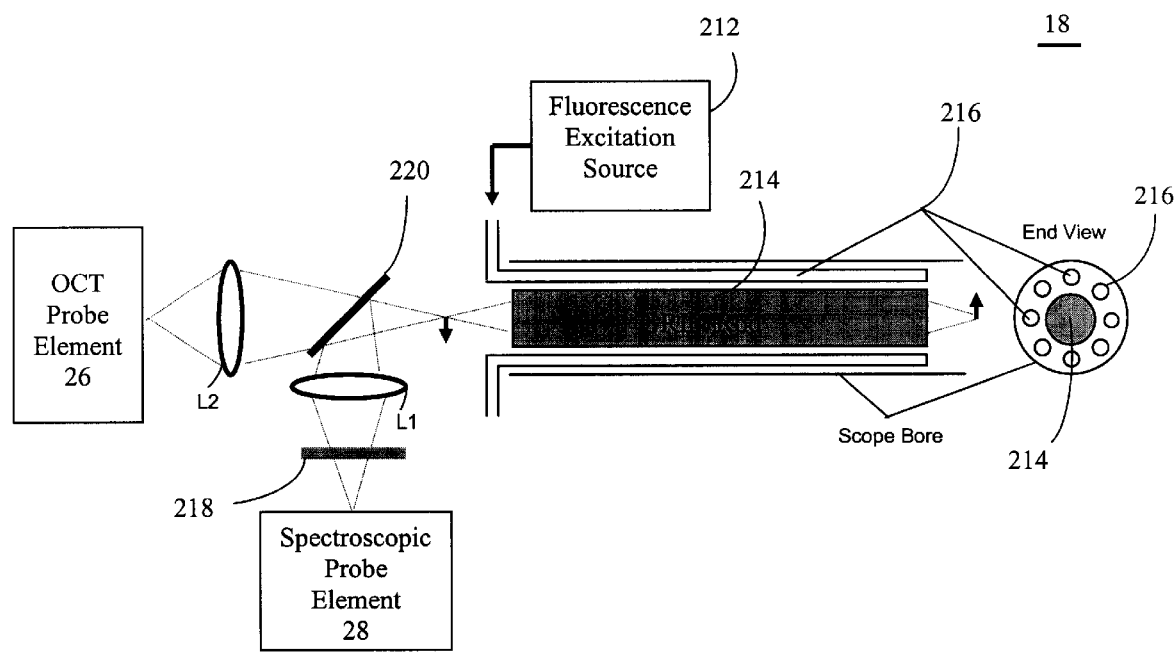
FIG. 4 is an embodiment of the optical system of FIG. 1 according to the present invention wherein the excitation radiation of the OCT and fluorescence probes are combined prior to being input into an endoscope probe.

FIG. 4 illustrates another embodiment of the present invention. In this embodiment, OCT and spectroscopic information may be obtained simultaneously or sequentially using the an OCT/Spectroscopic probe 18. Here, information from the OCT and spectroscopic imaging systems are combined prior to inclusion in an OCT/spectroscopic probe 18. In this embodiment, the spectroscopic information is fluoroscopic information.

OCT/spectroscopic probe 18 includes fluorescence excitation source 212 and a centrally located GRIN (gradient refractive index) relay lens 214 surrounded by an array of optical fibers 216 with high UV/visible transmission characteristics. The GRIN relay lens 214 provides a high quality, low cost component for use in imaging visual, fluorescence, or OCT data from the probe 18. The circumferentially located optical fibers 216 deliver UV radiation for fluorescence imaging and white light for direct visualization of the target tissue. Backscattered fluorescence from the tissue is imaged with the GRIN relay lens 214. GRIN relay lens 214 functions as a relay/objective in this embodiment.

In a preferred embodiment, OCT/spectroscopic probe 18 is a forward imaging type endoscope for fluorescence or visual imaging and endoscopic OCT imaging. It should be noted that any suitable endoscope formulation may be employed so long as the endoscope is capable of relaying fluorescence and OCT information once combined into and out of the GRIN relay lens 214. In this regard, an endoscope is a medical instrument used to view inside the human body by inserting the instrument into a natural or created aperture or cavity. The endoscope may use a coherent fiber optic bundle or conventional optics to relay the image to the operator, physician or television camera. Illumination is provided by concentric bundle of non-coherent fiber optics. The optical train tends to consist of an objective lens, a relay lens system which may be repeated as necessary, and an eyepiece lens system.

OCT/spectroscopic probe 18 further includes user selectable/replaceable filters 218 and a beam splitter 220. Selectable/replaceable filters 218 allow selection of which fluorescence wavelengths are imaged. Beam splitter 220 functions much like the optical filter 36 of FIG. 2. In this regard, dichroic reflective properties of the beam splitter 220 pass the NIR radiation to/from the OCT imaging probe element 26 for OCT imaging, but reflects fluorescent photons for example visible and/or ultraviolet radiation to the spectroscopic probe element 28. OCT imaging is accomplished via a scanned single mode fiber. Lens L2 in conjunction with the GRIN relay lens 214 image the small single mode fiber spot onto the target plane.

Thus, the OCT/spectroscopic probe 18 of FIG. 4, like the probe 18 of FIG. 2, may be employed to rapidly and non-invasively scan an area for spectroscopically-detected biochemical anomalies using spectroscopic (e.g., fluorescence) imaging (via probe 18, spectroscopic imaging system 12, and data analysis unit 16) and concurrently examine detailed morphology of any suspicious tissue (via probe 18, OCT system 14 and data analysis unit 16). The configuration of the optical elements in the OCT/spectroscopic probe 18 of FIG. 4, including beam splitter 220, allows an operator to concurrently and simultaneously image using OCT and fluorescence. The OCT/spectroscopic probe 18 allows simultaneous fluorescence images to be taken and OCT scans to be performed without movement of OCT/spectroscopic probe 18 relative to the tissue under investigation and without movement of optical components within the OCT/spectroscopic probe 18.

The present invention has been described by way of specific exemplary embodiments, and the many features and advantages of the present invention are apparent from the written description. While this invention has been described in connection with what is presently considered to be the most practical and/or preferred embodiments, it is to be understood that the invention is not limited to the disclosed embodiments. To the contrary, it is intended that various modifications within the spirit and scope of the appended claims are covered. In this regard, those skilled in the art will recognize that the present invention may be implemented by combining an OCT imaging system as described above in conjunction with a near-infrared (NIR) absorption spectroscopy measurement system. Under this circumstance, the optical imaging device would be used in the same mode of practice as described above to obtain both biochemical (via NIR spectroscopy) information and morphological (via OCT imaging) information. The present invention may also be implemented by combining an OCT imaging system as described above in conjunction with nearinfrared (NIR) reflectance spectroscopy measurement system. Under this circumstance, the optical imaging device would be used in the same mode of practice as described above to obtain both biochemical (via NIR spectroscopy) information and morphological (via OCT imaging) information.

The present invention may also be implemented using Raman spectroscopy measurement system. Here, the optical imaging device would be used in the same mode of practice as described above to obtain both biochemical (via Raman spectroscopy) information and morphological (via OCT imaging) information. In another embodiment, the present invention may be implemented using magnetic resonance (MR) spectroscopy measurement system. Under this circumstance, the imaging device would use an appropriately magnetic resonance sensitive radio frequency coil to obtain both biochemical (via MR spectroscopy) information and morphological (via OCT imaging) information. Moreover, the present invention may employ either fluorescence spectroscopy or NIR absorption spectroscopy or NIR reflectance spectroscopy or Raman spectroscopy or MR spectroscopy or any combination of the above in a system which is not endoscopically based, for example a system to explore or detect the presence of cancerous tissue at a skin lesion site or an intraoperatively available site.

In addition, the OCT imaging probe may be combined with a means for sensing spatial temperature information (for example, IR imaging camera). Such information may pertain to the biochemical or immunologic responses in the tissue. Under this circumstance, the optical elements in the endoscope may be modified to accommodate the passband of radiation appropriate for temperature measurements. A filter may also be included to enhance the sensitivity of the system to temperature indicating radiation.

In addition to implementing various imaging modalities, the present invention may be employed or incorporated in a catheter based approach for monitoring the intraluminal walls of arteries, veins, gastrointestinal structures, urinary structures, and reproductive structures. The present invention is one in which spectroscopic information which is combined with information from OCT images originates either from the native tissue components such as collagen, etc. or from the use of contrast agents that selectively enhance the spectroscopic signature of the targeted tissue. The contrast agents could be fluorescence dyes such as hematoporhyrin derivative or Raman enhancing dyes or agents. Furthermore, optical contrast agents could be used to change scattering and/or absorption properties of the targeted tissue thus changing both the OCT images as well as the spectroscopic data.

What is claimed is:

1. An optical imaging probe to provide information representative of morphological and biochemical properties of a sample, the optical imaging probe comprising:
    a spectroscopic imaging probe element,
    an OCT imaging probe element;
    an optical probe window; and
    a reflective optical filter disposed within an optical path between the optical window and the spectroscopic and OCT imaging probe elements and positioned to receive radiation incident on the optical probe window and to provide radiation of a first wavelength to the spectroscopic imaging probe element and to provide radiation of a second wavelength to the OCT imaging probe element, wherein the first wavelength is different than the second wavelength.

2. The optical imaging probe of claim 1 herein the optical imaging probe allows sequential imaging using the spectroscopic imaging probe element and the OCT imaging probe element.

3. The optical imaging probe of claim 1 wherein the optical imaging probe allows concomitant imaging using the spectroscopic imaging probe element and the OCT imaging probe element.

4. The optical imaging probe of claim 1 wherein the spectroscopic imaging probe element is used in a system selected from the group consisting of a fluorescence imaging system, an autofluorescence imaging system, a NIR absorption spectroscopic system, a NIR reflectance spectroscopic system, a Raman spectroscopic imaging system, a magnetic resonance imaging system, and an infrared system.

5. The optical imaging probe of claim 1 wherein the spectroscopic imaging probe element is a forward imaging type endoscope.

6. The optical imaging probe of claim 1 wherein the first wavelength is less than about 700 nm.

7. The optical imaging probe of claim 1 wherein the second wavelength is greater than about 700 nm.

8. The optical imaging probe of claim 1 wherein the first wavelength is in the NIR wavelength range.

9. The optical imaging probe of claim 1 wherein the reflective optical filter comprises a moveable mirror.

10. The optical imaging probe of claim 1 wherein the reflective optical filter provides a substantial amount of radiation of the first wavelength to the spectroscopic imaging probe element and wherein the first wavelength is less than about 700 nm.

11. The optical imaging probe of claim 1 wherein the reflective optical filter provides a substantial amount of radiation of the second wavelength to the OCT imaging probe element and wherein the second wavelength is greater than about 700 nm.

12. The optical imaging probe of claim 1 wherein the reflective optical filter reflect radiation of the first wavelength and transmits radiation of the second wavelength.

13. An optical imaging probe to provide information representative of morphological and biochemical properties of a sample, the optical imaging probe comprising:
    a spectroscopic imaging probe element;
    an optical probe window; and
    a means for receiving radiation incident on the optical probe window and for selectively providing radiation of a first wavelength to the spectroscopic imaging probe element and selectively providing radiation of a second wavelength to an OCT imaging probe element.

14. The optical imaging probe of claim 13 further comprising an OCT imaging probe element wherein the optical imaging probe allows sequential imaging using the spectroscopic imaging probe element and the OCT imaging probe element.

15. The optical imaging probe of claim 13 further comprising an OCT imaging probe element wherein the optical imaging probe allows concomitant imaging using the spectroscopic imaging probe element and the OCT imaging probe element.

16. The optical imaging probe of claim 13 wherein the first wavelength is less than about 700 nm and the second wavelength is greater than about 700 nm.

17. The optical imaging probe of claim 13 wherein the first wavelength is in the NIR wavelength range.

18. The optical imaging probe of claim 13 wherein the means for selectively providing radiation of a first wavelength to the spectroscopic imaging probe element provides a substantial amount of radiation of the first wavelength to the spectroscopic imaging probe element and wherein the first wavelength is less than about 700 nm.

19. The optical imaging probe of claim 13 wherein the means for selectively providing radiation of a second wavelength to the OCT imaging probe element provides a substantial amount of radiation of the second wavelength to the OCT imaging probe element and wherein the second wavelength is greater than about 700 nm.

20. A method for non-invasively sensing biochemical and morphological characteristics of a target tissue comprising:
    providing optical radiation to the target tissue;
    receiving optical radiation from the target tissue, wherein the optical radiation received from the target tissue contains information about the biochemical and morphological characteristics of the target tissue;
    selectively providing a first portion of the received optical radiation to a first optical imaging system, wherein the first portion of the received optical radiation comprises a first wavelength range; and
    selectively providing a second portion of the received optical radiation to a second optical imaging system, wherein the second portion of the received optical radiation comprises a second wavelength range.

21. The method of claim 20 wherein the first optical imaging system is a spectroscopic imaging system.

22. The method of claim 21 wherein the spectroscopic imaging system is used in a system selected from the group consisting of a fluorescence imaging system, an autofluorescence imaging system, a NIR absorption spectroscopic system, a NIR reflectance spectroscopic system, a Raman spectroscopic imaging system, a magnetic resonance imaging system, and an infrared system.

23. The method of claim 20 wherein the first wavelength range comprises radiation having wavelengths in the NIR wavelength range.

24. The method of claim 20 wherein the second optical imaging system is an OCT imaging system.

25. The method of claim 20 wherein the first wavelength range comprises radiation having wavelengths tat are less than about 700 nm.

26. The method of claim 20 wherein the second wavelength range comprises radiation having wavelengths which are greater than about 700 nm.

27. The method of claim 20 wherein selectively providing a first portion of the received optical radiation to a first optical imaging system is performed by a reflective optical filter disposed within a path of the received optical radiation.

28. The method of claim 27 wherein the reflective optical filter provides a substantial amount of radiation of the first wavelength range of the optical radiation received from the target tissue to a spectroscopic imaging system and wherein the first wavelength is less than about 700 nm.

29. The method of claim 27 wherein selectively providing a second portion of the received optical radiation to a second optical imaging system is performed by the reflective optical filter, and wherein the reflective optical filter provides a substantial amount of radiation of the second wavelength range of the optical radiation received from the target tissue to a OCT imaging system.

30. The method of claim 27 wherein the first wavelength range comprises radiation having wavelengths in the NIR wavelength range.

31. The method of claim 20 wherein the target tissue comprises a lesion, a tumor, or plaque.

32. The method of claim 20 wherein the target tissue is selected from the group consisting of skin, dental tissue, and cervical tissue.

33. A method for non-invasively sensing biochemical and morphological characteristics of a target tissue, the method comprising:
  screening the target tissue using an optical imaging system having a spectroscopic imaging modality and an OCT imaging modality, the optical imaging system comprising:
    a spectroscopic imaging system;
    an OCT imaging system;
    a data analysis unit; and
    an OCT/spectroscopic imaging probe comprising:
      a spectroscopic imaging probe element;
      an OCT imaging probe element;
      an optical probe window; and
      a reflective optical filter disposed within an optical path between the optical probe window and the spectroscopic and OCT imaging probe elements and positioned to receive radiation incident on the optical probe window and to selectively provide radiation of a first wavelength to the spectroscopic imaging probe element and to selectively provide radiation of a second wavelength to the OCT imaging probe element;
  detecting specific regions of interest in the target tissue using the spectroscopic imaging modality; and
  obtaining information about the morphological characteristics of those specific regions of interest using the OCT imaging modality.

34. The method of claim 33 wherein the first wavelength is in the NOR wavelength range.

35. The method of claim 33 wherein the first wavelength is less than about 700 nm.

36. The method of claim 33 wherein the second wavelength is greater than about 700 nm.

37. The method of claim 33 wherein the target tissue comprises a lesion, a tumor, or plaque.

38. The method of claim 33 wherein the target tissue is selected from the group consisting of skin, dental tissue, and cervical tissue.

* * * * *

UNITED STATES PATENT AND TRADEMARK OFFICE
CERTIFICATE OF CORRECTION

PATENT NO. : 6,507,747 B1 Page 1 of 1
DATED : January 14, 2003
INVENTOR(S) : Gowda et al.

It is certified that error appears in the above-identified patent and that said Letters Patent is hereby corrected as shown below:

Title page,
Item [75], Inventors, please delete "College Station, TX" and insert -- Houston, TX --; and please delete "Bryan, TX" and insert -- Pearland, TX --;
Item [56], References Cited,
U.S. PATENT DOCUMENTS, insert: -- 5,321,501  06/14/94  Swanson et al. --; and -- 5,459,570  10/17/95  Swanson et al. --;
FOREIGN PATENT DOCUMENTS, insert: -- 0815801  01/07/98  EPO --; and WO 98/38907  09/11/98  PCT --;
OTHER PUBLICATIONS, insert: -- Boppart et al., "Forward-Imaging Instruments for Optical Coherence Tomography," *Optics Letters*,1997; *22*(21):1618-1620. --;
-- Tearney et al., "In Vivo Endoscopic Optical Biopsy with Optical Coherence Tomography," *Science*, 1997; *276*:2037-2039. --;

Column 11,
Line 22, please delete "herein" and insert -- wherein --;
Line 59, please delete "reflect" and insert -- reflects --;

Column 14,
Line 21, please delete "NOR" and insert -- NIR --.

Signed and Sealed this

Twelfth Day of August, 2003

JAMES E. ROGAN
*Director of the United States Patent and Trademark Office*